United States Patent [19]

de Maybaum

[11] 4,328,460
[45] May 4, 1982

[54] INSTRUMENT INDICATOR OF THE PROLIFERATION MAGNITUDE IN A TANK

[76] Inventor: Blanca M. R. de Maybaum, Corrientes 2885, Piso 8° Dtc., 76 Buenos Aires, Argentina

[21] Appl. No.: 100,181

[22] Filed: Dec. 4, 1979

[51] Int. Cl.³ .............................................. G01R 27/14
[52] U.S. Cl. .................................... 324/64; 23/230 B; 204/195 B; 324/65 R
[58] Field of Search ............... 324/64, 65 R; 435/291, 435/817; 204/195 B; 23/230 B

[56] References Cited

U.S. PATENT DOCUMENTS

| | | | |
|---|---|---|---|
| 3,331,021 | 7/1967 | Marsh et al. | 324/65 R X |
| 3,365,663 | 1/1968 | Yamaguchi | 324/64 |
| 3,743,581 | 7/1973 | Cady et al. | 324/65 R UX |
| 3,890,201 | 6/1975 | Cady | 435/291 |
| 4,072,578 | 2/1978 | Cady et al. | 435/291 |
| 4,160,205 | 7/1979 | Hobbs et al. | 324/65 R |

OTHER PUBLICATIONS

Curtis et al., 4—Point Probe Measurement, IBM Technical Disclosure Bulletin, Nov. 1970, p. 1697.

Primary Examiner—Stanley T. Krawczewicz
Attorney, Agent, or Firm—Emory L. Groff, Jr.

[57] ABSTRACT

A device is provided which measures the degree of microbiological proliferation in water-fuel systems. By means of a simple electrochemical device including a trielectrodic plug having a work electrode, a reference electrode and a counter electrode, the level of microbial growth attained in a tank is determined in few seconds instead of several days usually needed for microbiological analysis.

1 Claim, 4 Drawing Figures

INSTRUMENT INDICATOR OF THE PROLIFERATION MAGNITUDE IN A TANK

The present invention relates to an instrument for indicating the degree of microbiological proliferation in a tank.

As it is known, in military and civil aviation, the moment at which the corrosion of the walls of a fuel tank (ground or aircraft fuel tank) begins creates a dangerous situation which is not readily determinable. The same danger occurs with regard to the potential risk of filter blockage in turbines of airplanes.

The corrosion referred to is due to the direct or indirect action of the microorganisms—particularly the fungus *Cladosporium resinae* (possibly through the metabolites it produces, etc., etc.)—on the walls of the tank. Such microorganisms which originate from determined conditions of stagnation and temperature begin to proliferate in continuous or discrete regions at the interface of the water-fuel which inevitably follows the water decantation after refueling the respective tank.

The spores normally contaminate the fuel but in the mentioned conditions they originate fungal mats causing corrosion and eventually filter blockage in turbines.

Accordingly, two successive conditions states may be recognized in the liquid fuel with respect to the corrosion of the walls of the tank where it is contained: (a) the "contamination" (by spores) existing in the fuel at the time of refueling, which may be quantitatively determined, to say, to be measured by the number of spores by mililiter ("degree of contamination"), and (b) the "proliferation" (of fungus) caused by the "contamination" (that is to say by spores), which cannot be quantitatively determined through a volumetric or gravimetric mean value, but only estimated by comparison ("degree of proliferation") visual test, mucilaginous consistency, etc. This gives rise to a low accuracy measurement through its effects as, for example percentage of bottom area and surrounding areas of the tank, frequency of filter blockage of aircraft turbines due to mucilaginous consistency of fungal mats, fortuitous failures in capacitive fuel gauges of fuel level etc., excluding those cases where the presence of water free of proliferation may introduce by itself dielectric perturbations). All the above conditions with regard to corrosion, are paraphrased respect to the possibility of initiation of filter blockage, originated by the colonies of microorganisms.

As a result of the above discussions there is no existing means for measuring either the degree of microbial proliferation affecting corrossiveness or filter blocking action in a liquid fuel. The actual procedures are by visual observation, in which case the tank must be empty, or by microbiological analysis, but in the latter case several days of incubation are required for determining the result.

This is fundamentally due to the lack of any known theoretical or empirical law which indicates the variation of the fungal proliferation in a tank as a function of the degree of fuel contamination by the contained spores.

Even if such theoretical or empiracal law existed, its application would not be sufficient to foresee the risk of initiation of corrosion in the tank and/or filter blockage, because that measurement, in case it were possible, could only give values of the probability of proliferation, it being impossible foresee any new parameters of measurement.

By the way, even if such a law were discovered, the measurements would need all of the necessary steps for determining not only the microbial proliferation but previously the degree of contamination on which it would be based, all of which would require a prohibitive amount of time for aero-navigation possibilities.

In the past there has not only been the lack of a measurement method for the measurement of microbial proliferation affecting the security of the plane, but also there has been a lack of a technique which, even if that measurement were possible, could indicate to the pilot in a given instant, in the airport or base, or during the flight, the degree of the risk due to the possibility of microbial proliferation and of its imminence. The lack of such technique hinders detection of the presence or absence of microbial proliferation in the fuel and the relative.

The primary object of the present invention consists in providing a control device particularly appropriate to indicate in a quick and direct way the degree of microbial inminence of proliferation in a jet fuel tank, visualizable by the pilot or by the ground crew.

According to the research work performed which lead to the present invention, it was surprisingly discovered that at each fungal proliferation degree (probability proportional to the metabolites concentration generated by themselves), for a given applied potential corresponds a circulatory current intensity in the liquid between the respective electrodes.

In that sense, according to the present invention, a means for estimating the amount of microbial proliferation is given by a rate of current intensities which, being indicated by the needle of an ammeter, would give not the exact numerical value but a zone indicating the degree of proliferation in the tank at a given instant.

Nevertheless, the measurement of those current intensities cannot be performed in a conventional way, but by means of a triad of electrodes of similar structural constructive characteristics for obtaining the desired measurement. The apparatus would thus function as a galvanoscope more than as an ammeter.

According to the present invention the mentioned trielectrodic set comprises by: (a) a work electrode, (b) a reference electrode, (c) a counter electrode.

Since the objective of the proposed device consists of providing a detector instrument of the order of the electric current intensity circulating between the work electrode and the counter electrode, for a given tension of the work electrode selectively adopted respect to that of the reference one, it is required that this reference electrode be designed in such a form and concentration that its potential be invariable. With that purpose in mind, the present invention proposes that this potential be defined by a given electrochemical reaction.

The work electrode could preferably be made of aluminium or an aluminium alloy. With regard to the counter electrode it could preferably be made of platinum or stainless steel.

The foregoing and other objects and advantages will become apparent to those skilled in the art from the following description of a preferred embodiment of the invention as illustrated in the accompanying drawing wherein.

Similar reference characters designate corresponding parts throughout the several views of the drawing.

Figure 1:
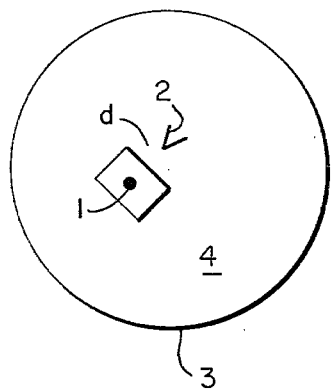
FIG. 1 is a schematic top view of the trielectrodic plug.

Referring to the drawings in detail, the trielectrodic plug comprises a work electrode 1, a reference electrode 2 and a counter electrode 3, whose respective axes are normal to the insulating material 4 to which they are fixed (FIG. 1).

Figure 2:
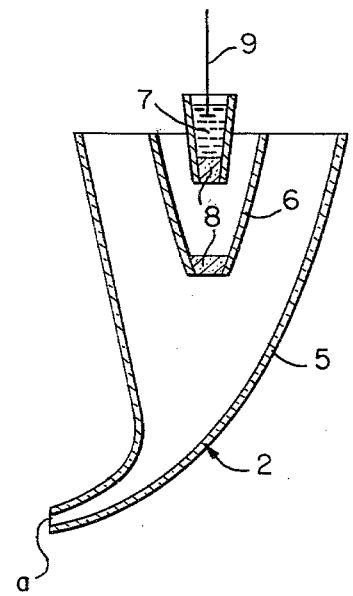
FIG. 2 is a fragmentary vertical cross section of the reference electrode.

The reference electrode 2 can be more clearly seen in FIG. 2, where it is shown that it consists of a glass container 5 which is substantially vertical and whose lower tip is a substantially circular hole a, being spaced distance d from the electrode 1 (FIG. 1) such distance being less than its diameter. Preferably, distance d should be less than 0.5 mm. and the diameter of the hole is 1 mm.

In the container 5 is placed a second container 6 and in this container, a third container 7 is placed. The last two containers are closed by respective porous plates 8.

The reference electrode 2 (FIG. 2) has an in equilibrium chemical reaction with definite electrochemical potential, appropriate to act as a reference electrode.

Its composition consists of mercury (Hg), (liquid), calomel ($Cl_2Hg_2$) (solid) and cloride solution ($Cl^-$). The Hg and calomel are poured in the container 7, in which the electric conductor 9 is placed. The cloride solution is contained in container 6 while the analyzed water is placed in the container 5.

Figure 3:
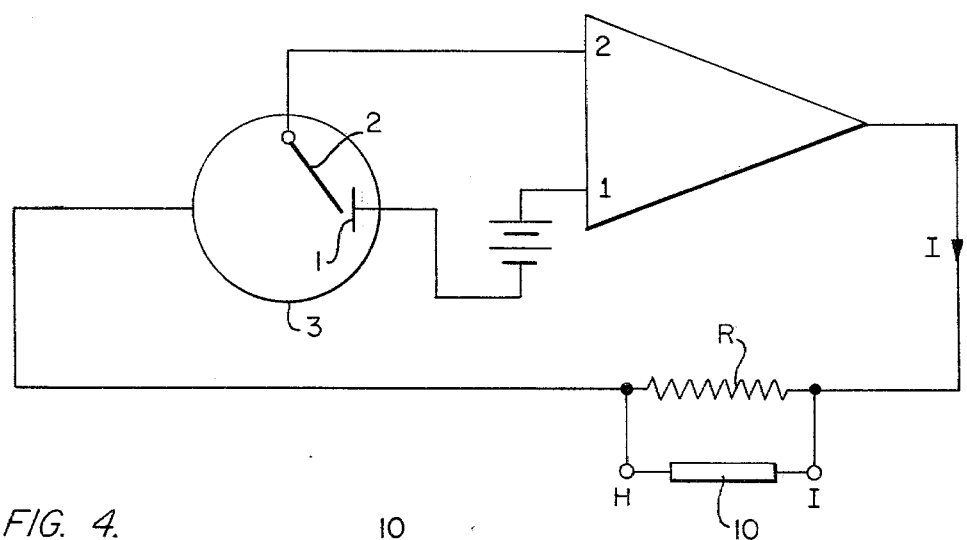
FIG. 3 is a schematic view of the device.
Figure 4:
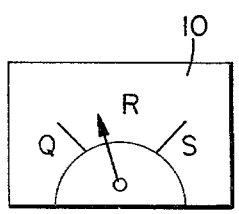
FIG. 4 is a schematic illustration of the measuring instrument.

The device is completed by a direct current source and an operational amplifier which, together with the tri-electrodic set defines a potentiostatic circuit including a resistance R through which is connected, as a shunt between H and I, a needle instrument 10 (FIG. 3), sensitive to the electric current, whose field of measurement is divided in three zones Q, R, S. This instrument will be placed in the instrument board of the plane cabin.

Previous to the division of the field into those three zones, the apparatus must be adjusted so as to make each range of current intensity correspond to a degree of microbial proliferation, as follows: Q=normal, R=incipient, S=dangerous.

What I claim is:

1. An indicator device for the quick and direct determination of the degree of microbiological proliferation in fuel systems having a water-fuel interface, such as a jet fuel tank particularly adapted for being visually inspected by the pilot or by a maintenance crew on the ground; characterized by a trielectrodic plug comprising a work electrode (1), a reference electrode (2) and a counter electrode (3), completed by a DC source and an operational amplifier, which defines a potentiostatic circuit, including an electric resistance through which is connected, as a shunt, an instrument sensitive to the electric current, whose field of measurement is divided into three zones, corresponding to three different degrees of proliferation: Q=normal, R=incipient and S=dangerous.

* * * * *